United States Patent
Okamoto et al.

(10) Patent No.: US 7,402,384 B2
(45) Date of Patent: Jul. 22, 2008

(54) METHODS FOR EVALUATING PROBE ARRAYS

(75) Inventors: Tadashi Okamoto, Kanagawa (JP); Nobuko Yamamoto, Kanagawa (JP); Tomohiro Suzuki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 293 days.

(21) Appl. No.: 10/634,510

(22) Filed: Aug. 4, 2003

(65) Prior Publication Data

US 2004/0018552 A1  Jan. 29, 2004

Related U.S. Application Data

(63) Continuation of application No. 09/988,873, filed on Nov. 21, 2001, now abandoned.

(30) Foreign Application Priority Data

Nov. 24, 2000  (JP) ............................ 2000-357446

(51) Int. Cl.
*C12Q 1/68*  (2006.01)
*C12M 1/36*  (2006.01)
*C07H 21/04*  (2006.01)

(52) U.S. Cl. .................. 435/6; 435/287.2; 536/23.1; 536/25.3

(58) Field of Classification Search .................. None
See application file for complete search history.

(56) References Cited

U.S. PATENT DOCUMENTS

| | | | | |
|---|---|---|---|---|
| 5,445,966 A | 8/1995 | Giese et al. | ................. | 436/109 |
| 5,474,796 A | 12/1995 | Brennan | .................... | 427/2.13 |
| 5,556,752 A | 9/1996 | Lockhart et al. | ................ | 435/6 |
| 5,670,315 A | 9/1997 | Yamamoto et al. | ............. | 435/6 |
| 5,843,655 A * | 12/1998 | McGall | .......................... | 435/6 |
| 6,013,789 A | 1/2000 | Rampal | ..................... | 536/25.3 |
| 6,083,763 A | 7/2000 | Balch | ......................... | 436/518 |
| 6,090,933 A * | 7/2000 | Kayyem et al. | ............. | 536/25.3 |
| 6,245,518 B1 * | 6/2001 | Baier | ............................. | 435/6 |
| 6,251,583 B1 | 6/2001 | Zhang et al. | .................. | 435/5 |
| 6,284,465 B1 * | 9/2001 | Wolber | .......................... | 435/6 |
| 6,312,906 B1 * | 11/2001 | Cass et al. | ..................... | 435/6 |
| 6,403,319 B1 | 6/2002 | Lizardi et al. | .................. | 435/6 |
| 6,469,151 B1 | 10/2002 | Egholm et al. | ............. | 536/23.1 |
| 6,471,916 B1 * | 10/2002 | Noblett | .................... | 422/82.08 |
| 6,869,763 B1 * | 3/2005 | Tamura et al. | ................. | 435/6 |

FOREIGN PATENT DOCUMENTS

| | | |
|---|---|---|
| WO | 00/34523 | 6/2000 |
| WO | 00/47767 | 8/2000 |

* cited by examiner

*Primary Examiner*—B J Forman
(74) *Attorney, Agent, or Firm*—Fitzpatrick, Cella, Harper & Scinto

(57) ABSTRACT

A probe array comprises a plurality of probes immobilized at a plurality of matrix sites on a substrate for capturing a target substance, wherein the probes are sequentially synthesized at the matrix sites on the substrate until a desired length, the probes are different from each other, and a labeling compound is coupled to each terminus of the probes in a final step of the synthesis. The probe array of the invention allows sensitive and reliable detection of the target substance. A method of evaluating the amount of the fully synthesized probes at respective matrix sites is also provided.

2 Claims, 7 Drawing Sheets

FIG. 4

| 700 | 400 | 3290 | 880 | ND | ND | 230 | ND |
| --- | --- | --- | --- | --- | --- | --- | --- |
| 1130 | 900 | 3250 | 1070 | ND | ND | 250 | ND |
| 3090 | 780 | 3950 | 2470 | 3780 | 1500 | 4100 | 1170 |
| 660 | 1500 | 2500 | 1610 | ND | ND | 260 | ND |
| ND | ND | 640 | ND | ND | ND | 230 | ND |
| ND | ND | 790 | ND | ND | ND | 290 | ND |
| 2010 | 1660 | 4030 | 2280 | 1570 | 1910 | 2380 | 860 |
| ND | ND | 660 | ND | ND | ND | 600 | ND |

| | | | | | | | |
|---|---|---|---|---|---|---|---|
| 1190 | 940 | 4550 | 1270 | ND | ND | 520 | ND |
| 1830 | 1970 | 4460 | 1440 | ND | ND | 330 | ND |
| 5270 | 1600 | 6630 | 5180 | 4190 | 2680 | 6030 | 2570 |
| 1390 | 2160 | 5570 | 1840 | ND | ND | 500 | ND |
| ND | ND | 1240 | ND | ND | ND | 640 | ND |
| ND | ND | 1150 | ND | ND | ND | 810 | ND |
| 2740 | 3290 | 4700 | 3130 | 2650 | 3230 | 3940 | 1590 |
| ND | ND | 1340 | ND | ND | ND | 1120 | ND |

| 1050 | 590 | 3780 | 910 | ND | ND | 420 | ND |
| --- | --- | --- | --- | --- | --- | --- | --- |
| 1310 | 1320 | 3270 | 1240 | ND | ND | 230 | ND |
| 4560 | 1150 | 4830 | 4010 | 3040 | 1800 | 4380 | 1810 |
| 1220 | 1540 | 4130 | 1240 | ND | ND | 400 | ND |
| ND | ND | 940 | ND | ND | ND | 590 | ND |
| ND | ND | 980 | ND | ND | ND | 560 | ND |
| 2040 | 2550 | 3840 | 2500 | 1890 | 2490 | 2890 | 1130 |
| ND | ND | 920 | ND | ND | ND | 960 | ND |

FIG. 7

| | | | | | | | |
|---|---|---|---|---|---|---|---|
| 0.86 | 1.21 | 0.91 | 1.06 | ND | ND | 0.94 | ND |
| 1.06 | 1.13 | 1.03 | 0.88 | ND | ND | 1.09 | ND |
| 0.88 | 1.05 | 1.04 | 0.98 | 1.05 | 1.03 | 1.04 | 1.08 |
| 0.86 | 1.06 | 1.04 | 1.12 | ND | ND | 0.94 | ND |
| ND | ND | 1.00 | ND | ND | ND | 0.82 | ND |
| ND | ND | 0.89 | ND | ND | ND | 1.10 | ND |
| 1.02 | 0.98 | 0.93 | 0.95 | 1.06 | 0.98 | 1.03 | 1.06 |
| ND | ND | 1.11 | ND | ND | ND | 0.89 | ND |

SEQUENCE LISTING

<160> NUMBER OF SEQ ID NOS: 65

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 1

-continued

```
gatgggactc aagttcat                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 2
gatgggactc aggttcat                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 3
gatgggactc acgttcat                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 4
gatgggactc atgttcat                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 5
gatgggactc gagttcat                                                 18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 6
gatgggactc gggttcat                                                 18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 7
gatgggactc gcgttcat                                                 18

<210> SEQ ID NO 8
<211> LENGTH: 18
<212> TYPE: DNA
```

```
<213> ORGANISM: Artificial Sequence
<220> FEATURE:
<223> OTHER INFORMATION: Description of Artificial Sequence:Synthesized

<400> SEQUENCE: 8
gatgggactc gtgttcat                                                    18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 9
gatgggactc cagttcat                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 10
gatgggactc cggttcat                                                    18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 11
gatgggactc ccgttcat                                                    18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 12
gatgggactc ctgttcat                                                    18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 13
gatgggactc tagttcat                                                    18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 14
gatgggactc tggttcat                                                    18
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 15
gatgggactc tcgttcat                                                 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 16
gatgggactc ttgttcat                                                 18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 17
gatggggctc aagttcat                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 18
gatggggctc aggttcat                                                 18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 19
gatggggctc acgttcat                                                 18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 20
gatggggctc atgttcat                                                 18

<210> SEQ ID NO 21
<211> LENGTH: 18
<212> TYPE: DNA
<213> ORGANISM: Artificial Sequence
<220> FEATURE:

<223> OTHER INFORMATION: Description of Artificial Sequence:Synthesized

<400> SEQUENCE: 21
gatggggctc gagttcat                                                 18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 22
gatggggctc gggttcat                                                 18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 23
gatggggctc gcgttcat                                                 18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 24
gatggggctc gtgttcat                                                 18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 25
gatggggctc cagttcat                                                 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 26
gatggggctc cggttcat                                                 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 27
gatggggctc ccgttcat                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 28
gatggggctc ctgttcat                                                 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 29
gatggggctc tagttcat                                                 18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 30
gatggggctc tggttcat                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 31
gatggggctc tcgttcat                                                 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 32
gatggggctc ttgttcat                                                 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 33
gatgggcctc aagttcat                                                 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:Synthesized -continued

<400> SEQUENCE: 34
gatgggcctc aggttcat                                                    18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 35
gatgggcctc acgttcat                                                    18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 36
gatgggcctc atgttcat                                                    18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 37
gatgggcctc gagttcat                                                    18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 38
gatgggcctc gggttcat                                                    18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 39
gatgggcctc gcgttcat                                                    18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 40
gatgggcctc gtgttcat                                                    18

<210> SEQ ID NO 41
<211> LENGTH: 18

```
<212> TYPE: DNA
<213> ORGANISM: Artificial Sequence
<220> FEATURE:
<223> OTHER INFORMATION: Description of Artificial Sequence:Synthesized

<400> SEQUENCE: 41
gatgggcctc cagttcat                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 42
gatgggcctc cggttcat                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 43
gatgggcctc ccgttcat                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 44
gatgggcctc ctgttcat                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 45
gatgggcctc tagttcat                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 46
gatgggcctc tggttcat                                                 18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 47
```
gatgggcctc tcgttcat                                                18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 48
gatgggcctc ttgttcat                                                18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 49
gatgggtctc aagttcat                                                18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 50
gatgggtctc aggttcat                                                18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 51
gatgggtctc acgttcat                                                18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 52
gatgggtctc atgttcat                                                18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 53
gatgggtctc gagttcat                                                   18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 54
gatgggtctc gggttcat                                                   18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 55
gatgggtctc gggttcat                                                   18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 56
gatgggtctc gtgttcat                                                   18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 57
gatgggtctc cagttcat                                                   18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 58
gatgggtctc cggttcat                                                   18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 59
gatgggtctc ccgttcat                                                   18

<210> SEQ ID NO 60
<211> LENGTH: 18
<212> TYPE: DNA

```
<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 60
gatgggtctc ctgttcat                                                   18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 61
gatgggtctc tagttcat                                                   18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 62
gatgggtctc tggttcat                                                   18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 63
gatgggtctc tcgttcat                                                   18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 64
gatgggtctc ttgttcat                                                   18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:Synthesized

<400> SEQUENCE: 65
atgaaccgga ggcccatc                                                   18
```

METHODS FOR EVALUATING PROBE ARRAYS

This application is a continuation of application Ser. No. 09/988,873, filed Nov. 21, 2001 now abandoned.

BACKGROUND OF THE INVENTION

1. Field of the Invention

The present invention relates to a labeled probe array, a method for producing the labeled probe array, and an method for determining the amount of a target substance using the labeled probe array.

2. Related Background Art

Recently, for precise assessment of a target substance, it has been intensively studied a method using a plurality of probes disposed in an array on the surface of a substrate, called "probe array". A typical example is a so-called "DNA probe array" in which a plurality of DNA probes are disposed on a substrate. This DNA probe array is also referred to as a DNA chip. By using the DNA probe array, for example, the presence of a plurality of target genes can be analyzed at the level of base sequence.

Methods of making the probe array are roughly classified into two.

One is a method that synthesizes probes by sequential synthesis on a solid substrate, applicable to the probes being a substance that can be synthesized by chemical elongation and of which nucleotide or amino acid sequence has an important meaning, e.g., DNA, oligonucleotide, peptide nucleic acids (PNAs), proteins, and oligopeptides.

As an example of such a method, U.S. Pat. No. 5,445,966 discloses a method of synthesizing a DNA probe array on a substrate by using photolytic protection groups and photolithography. Alternatively, U.S. Pat. No. 5,474,796 discloses a method supplying nucleotide monomers by an ink jet process.

The other method is applicable, in addition to the above described substances, to the substances not chemically synthesizable, since this method is to supply probes that have been previously synthesized or prepared to the matrix sites of a probe-array substrate by the micro-dispensing method, pin transfer method, or ink jet process etc.

Since the second method uses probes which have been purified and of which quantity can be controlled, the purity of the probes are secured and the concentrations of the probes to be reacted with the substrate can be freely determined. Consequently, the final amounts of respective probes on the substrate surface can be assessed with a certain accuracy, to enhance the reliability of the target substance detection using the probe array. On the other hand, the second method requires previous synthesis of all kinds of probes for the probe array and it also requires to apply the probes to the substrate for reaction. Sometimes, several hundreds of thousands of probes may be required for a probe array. In that case, it will be considerably difficult to synthesize all probes beforehand.

On the other hand, according to the first method, necessary probes are synthesized on the substrate and then used for the reaction with the target substances, so that operations for immobilizing the previously synthesized or prepared probes onto the substrate can be omitted.

However, in order to improve the detection sensitivity or reliability of the first method, following points must be improved.

(1) The yield in each step of the sequential synthesis is not 100%, some times the final yield is as low as 5%. This directly leads to reduction in the sensitivity when the target substance is detected.

(2) For the same reason, both full length probes and shorter length probes are present at each matrix site of the probe array. This lowers the reliability in detecting a target substance.

(3) As a result of in situ synthesis on the substrate, the amount of the probe at each matrix site cannot be measured. This also lowers the reliability in detecting a target substance.

(4) As mentioned above, the synthetic yield in each step of sequential synthesis is not 100% and the synthetic yield varies depending on the steps and the matrix sites, so that the final amounts of respective probes vary broadly. This also lowers the reliability of the detection of a target substance.

SUMMARY OF THE INVENTION

The object of the present invention is to solve the above described problems.

According to the present invention, there is provided a method of making a probe array for capturing a target substance which comprises the steps of:

synthesizing a plurality of probes immobilized at a plurality of matrix sites on a substrate by sequential synthesis where constitutional units are added one by one to a plurality of basal parts immobilized to the substrate until a desired length is obtained; and coupling a labeling compound to a terminus of the probe of the desired length.

Further, according to the present invention, there is provided a probe array which comprises a plurality of probes immobilized at a plurality of matrix sites on a substrate for capturing a target substance, wherein the probes are sequentially synthesized at the matrix sites on the substrate until a desired length, the probes are different from each other, and a labeling compound is coupled to each terminus of the probes in a final step of the synthesis.

The present invention also provides a method of measuring an amount of a probe in a probe array wherein the probe array comprises a plurality of probes immobilized at a plurality of matrix sites on a substrate for capturing a target substance, the probes are sequentially synthesized at the matrix sites on the substrate until a desired length, the probes are different from each other, and a labeling compound is coupled to each terminus of the probes in a final step of the synthesis, which method comprises the step of measuring an amount of the labeling compound at each matrix site.

The present invention provides a method of evaluating an amount of a target substance, which comprises the steps of:

reacting a probe array and a target substance wherein the probe array comprises a plurality of probes immobilized at a plurality of matrix sites on a substrate for capturing a target substance, the probes are sequentially synthesized at the matrix sites on the substrate until a desired length, the probes are different from each other, and a labeling compound is coupled to each terminus of the probes in a final step of the synthesis;

measuring an amount of the labeling compound at each matrix site to determine an amount of the probe at the matrix site;

measuring an amount of a labeled target substance captured by the probe at the matrix site; and comparing the amount of the probe with the amount of the labeled target substance.

The present invention also provides a method of evaluating an amount of a target substance comprising the steps of:

reacting a probe array and a target substance, wherein the probe array comprises a plurality of probes immobilized at a plurality of matrix sites on a substrate for capturing a target substance, the probes are sequentially synthesized at the matrix sites on the substrate until a desired length, the probes are different from each other, and a labeling compound is coupled to each terminus of the probes in a final step of the synthesis;

measuring an amount of the labeling compound at each matrix site to determine an amount of the probe at the matrix site;

measuring an amount of a labeled target substance captured by the probe at the matrix site;

measuring an amount of the labeling compound directly bonded to the substrate at a predetermined matrix site on the surface of the substrate during a first step of the sequential synthesis without elongation reaction; and comparing the amount of the probe, the amount of the labeled target substance, and the amount of the directly bonded labeling compound.

BRIEF DESCRIPTION OF THE DRAWINGS

FIG. 4 shows the hybridization result of Example 3;

FIG. 5 shows corrected result of the hybridization of Example 3;

FIG. 6 shows the hybridization result of Comparative Example; and

FIG. 7 shows a comparison of the result of FIG. 6 with the result of FIG. 5.

DETAILED DESCRIPTION OF THE PREFERRED EMBODIMENTS

Figure 1:
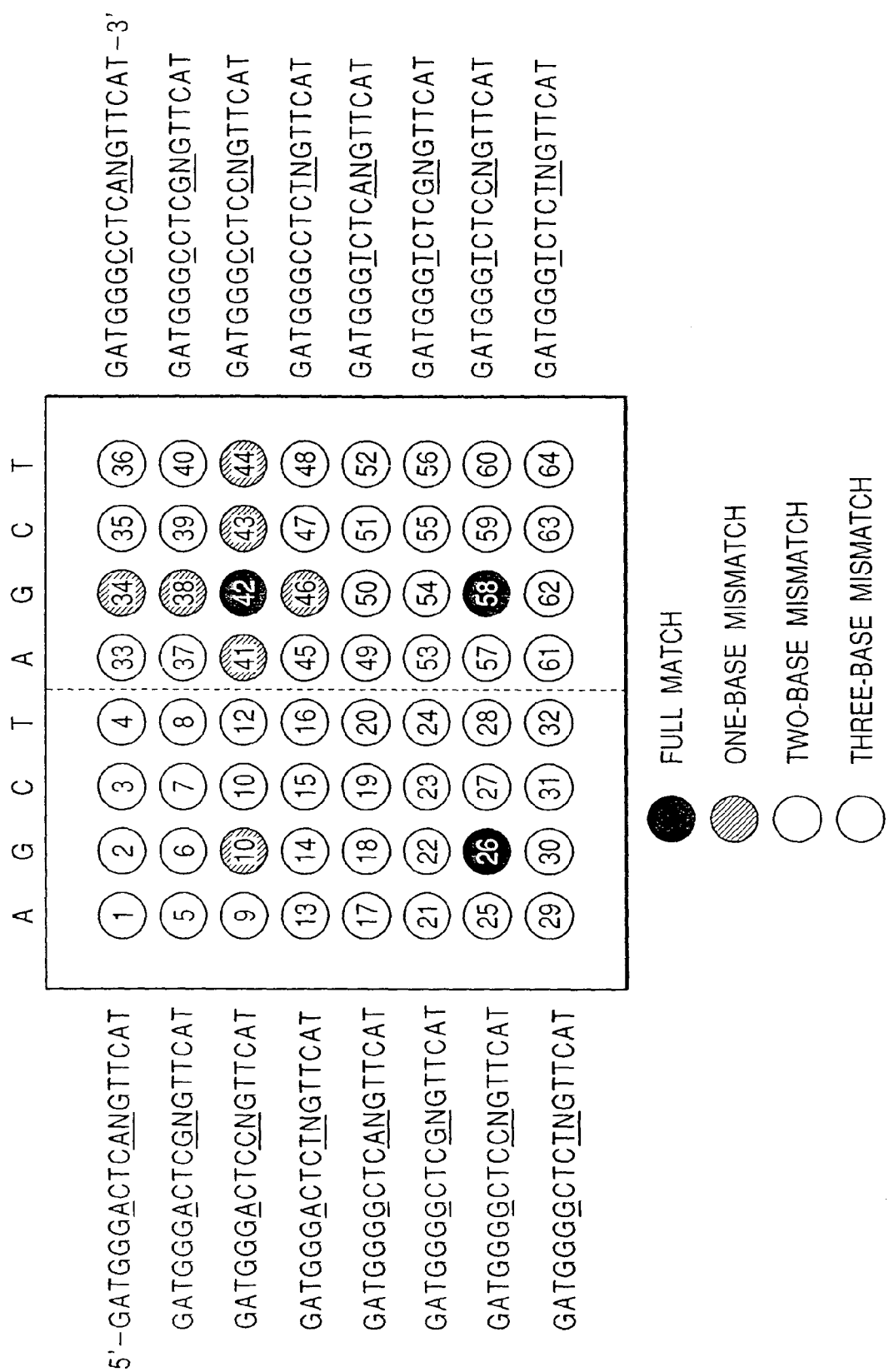
FIG. 1 shows an probe arrangement on the array substrate with nucleotide sequences of a target DNA and probes.

The feature of the present invention is to introduce a quantitatively determinable labeling substance to the probe in the final step of the sequential synthesis.

The sequential synthesis is a method for synthesizing a concatenate oligomer consisting of from several to around one hundred units (for example, DNA consisting of nucleotides and protein consisting of amino acid residues) by sequentially bonding the desired units. This conventional method widely used in synthesis of oligonucleotides, oligopeptides, and PNAs can be used in the present invention without any alterations thereto. In case of DNA (oligonucleotide) synthesis, for example, the most commonly used method with an automatic synthesizer at present is the phosphoramidite method. This method comprises the following steps of:

(1) deprotecting hydroxyl groups bonded to the surface of a solid carrier (a glass substrate etc.) via a linker;
(2) coupling the deprotected hydroxyl group to the 3' phosphorous group of an amidite monomer having a desired base;
(3) capping the hydroxyl groups not reacted in step (2);
(4) oxidizing the coupled amidite in step (3) from phosphite to phosphate;
(5) removing the protection group protecting 5' hydroxyl moiety of the coupled amidite in step (2);
(6) repeating steps (2) to (5) to obtain an oligonucleotide of a desired length and base sequence in a direction from 3' to 5'; and
(7) deprotecting the nucleotide bases.

Examples of the probes are, but not limited to, RNAs, DNAs, oligonucleotides, peptide nucleic acids (PNAs), proteins, oligopeptides or the like.

In detecting a target substance using the probe array, it is common to label the target substance with a fluorescent dye. Therefore, it is convenient to label the probes with a fluorescent dye, because the labeling substance can be detected by the same measuring device for detecting the target.

Other labeling substances may be used, but should be chosen not to disturb detection of the target substance. In this viewpoint, it is preferable that the labeling agent for the target substance and that for the probe are different.

When labeling substances are both fluorescent dyes, it is desirable that they are different in excitation wavelength and fluorescent wavelength. For example, one is FITC and the other is rhodamine, or one is CY3 (Amersham Pharmacia Biotech Co.) and the other is CY5 (Amersham Pharmacia Biotech Co.).

In sequential synthesis in the solid phase, capping (treatment to inactivate the uncoupled functional group) is carried out after each elongation reaction. For example, in a solid phase synthesis of DNA, hydroxyl groups at the reactive site are inactivated by acetylation.

Therefore, in the present invention, only probes that have elongated to the final step (to a desired chain length) are labeled with a labeling substance, so that the measurement of the amount of the labeling substance at each matrix site allows evaluation of the probe quantity at each matrix site.

Thus, relative correction between respective probes in determining the amount of the target substance can be done by comparing the quantitatively determined probe amount and the amount of the labeling substance of the target substance captured by the probe.

In order to determine the absolute amount of the captured target substance in the present invention, a control site is provided on the substrate where only the first hydroxyl groups introduced to the substrate are labeled with a labeling substance without subsequent elongation reaction steps, and the amount of the labeling substance at the control site is compared with the respective amounts of the labeling substance coupled to the probes synthesized at the matrix sites by elongation reaction. This allows to evaluate relative amounts of the synthesized probes to the initial functional groups introduced to the substrate surface. By comparing thus determined amount of the probe in each matrix with the amount of the labeling substance coupled to the target substance that was captured by the probe, evaluation of the absolute amount of the target substance and relative correction between the probes can be carried out simultaneously.

Any procedures disclosed in the above described U.S. Patents and other conventional techniques can be used for respective steps in preparing the terminal-labeled probe array of the present invention.

The present invention will now be particularly described by the following Examples.

EXAMPLE 1

Making of a Terminal Labeled DNA Probe Array (1) A synthetic quartz substrate (25.4 mm×25.5 mm×0.5 mm) was subjected to ultrasonication for 20 minutes with a 10% aqueous solution of a ultrasonic detergent (GP-II, a product of Branson Co.), washed with ultra pure water, dipped in an aqueous solution of 1 N sodium hydroxide (80° C.), washed with ultra pure water, dried, and then subjected to the UV ozone treatment to clean the surface thereof.

(2) Next, DEEP-UV resist containing carbon black (BK-739P, a negative photoresist for black matrix, Nippon Steel Chemical Co., Ltd.) was applied to the substrate to a thickness of 5 µm by using a spin coater. This substrate was heated at 80° C. for 5 minutes on a hot plate to pre-bake the resist. This resist film was subjected to proximity exposure by using a DEEP-UV aligner and a pattern mask corresponding to the matrix pattern where the matrix sites of 100 µm×100 µm are arranged at 100 μm intervals within an area of 1 cm×1 cm as shown in FIG. 1. Then the resist was developed with an inorganic alkaline aqueous solution in a spin developer, and rinsed with ultra pure water to completely remove the inorganic alkaline aqueous solution. This substrate was roughly dried with the use of a spin dryer, then heated to 180° C. for 30 minutes in a clean oven in order to post-bake the resist. Consequently, 2500 matrix sites, each of which being surrounded with the resist film, were formed on the surface of the substrate. The volume of each matrix site thus formed is calculated as 50 pL.

(3) An aqueous solution of 1% silane coupling agent having epoxy groups (KBM403: γ-glycidoxypropyltrimethoxysilane, Shin-Etsu Chemical Co., Ltd.) was hydrolyzed by stirring it for one hour at room temperature. The substrate provided with the above described matrix sites thereon was dipped in this solution for one hour and cleaned with ultra pure water properly, then heated at 120° C. for one hour. As a result, epoxy groups were bonded to the above described matrix sites. By treating the substrate with hexaethylene glycol, hydroxyl groups were introduced to the matrix sites for coupling oligonucleotides.

(4) The synthesis of oligonucleotides on the substrate was carried out by the ordinary phosphoramidite method. A polyethylene chamber to contain the above described substrate therein was fabricated and then mounted in a column part of a DNA synthesizer (381A, a product of ABI Inc.). Synthesizing steps other than substance application of amidite monomers and activators, subsequent cleaning, and drying steps were carried out by the DNA synthesizer. A modified piezo ink-jet system was employed in supplying the amidite monomers and activators. Operating the piezo ink-jet apparatus in a dry box (argon), not inks but acetonitrile solutions of four amidite monomers and an activator were applied to the above described matrix sites on the substrate under the position control. The liquid amount supplied at a time from the piezo device was 24 pL on average.

(5) Basically, it is possible to synthesize distinct oligonucleotides for all of 2500 matrix sites. In this example, however, 64 oligonucleotides, i.e., DNA probes, were synthesized. These 64 oligonucleotides include every base variation at three positions in two triplets encoding two amino acids in a carcinogenic gene p53. The DNA probe array substrate obtained was dipped in a 30% aqueous solution of ammonia for 12 hours at room temperature to deprotect the nucleic acid bases.

Base sequences of synthesized DNA probes (SEQ ID NO: 1 to SEQ ID NO: 64) are as follows.

```
No. 1.   5'-G A T G G G A C T C A A G T T C A T-3'
No. 2.   5'-G A T G G G A C T C A G G T T C A T-3'
No. 3.   5'-G A T G G G A C T C A C G T T C A T-3'
No. 4.   5'-G A T G G G A C T C A T G T T C A T-3'
No. 5.   5'-G A T G G G A C T C G A G T T C A T-3'
No. 6.   5'-G A T G G G A C T C G G G T T C A T-3'
No. 7.   5'-G A T G G G A C T C G C G T T C A T-3'
No. 8.   5'-G A T G G G A C T C G T G T T C A T-3'
No. 9.   5'-G A T G G G A C T C C A G T T C A T-3'
No. 10.  5'-G A T G G G A C T C C G G T T C A T-3'
No. 11.  5'-G A T G G G A C T C C C G T T C A T-3'
No. 12.  5'-G A T G G G A C T C C T G T T C A T-3'
No. 13.  5'-G A T G G G A C T C T A G T T C A T-3'
No. 14.  5'-G A T G G G A C T C T G G T T C A T-3'
No. 15.  5'-G A T G G G A C T C T C G T T C A T-3'
No. 16.  5'-G A T G G G A C T C T T G T T C A T-3'
No. 17.  5'-G A T G G G G C T C A A G T T C A T-3'
No. 18.  5'-G A T G G G G C T C A G G T T C A T-3'
No. 19.  5'-G A T G G G G C T C A C G T T C A T-3'
No. 20.  5'-G A T G G G G C T C A T G T T C A T-3'
No. 21.  5'-G A T G G G G C T C G A G T T C A T-3'
No. 22.  5'-G A T G G G G C T C G G G T T C A T-3'
No. 23.  5'-G A T G G G G C T C G C G T T C A T-3'
No. 24.  5'-G A T G G G G C T C G T G T T C A T-3'
No. 25.  5'-G A T G G G G C T C C A G T T C A T-3'
No. 26.  5'-G A T G G G G C T C C G G T T C A T-3'
No. 27.  5'-G A T G G G G C T C C C G T T C A T-3'
No. 28.  5'-G A T G G G G C T C C T G T T C A T-3'
No. 29.  5'-G A T G G G G C T C T A G T T C A T-3'
No. 30.  5'-G A T G G G G C T C T G G T T C A T-3'
No. 31.  5'-G A T G G G G C T C T C G T T C A T-3'
No. 32.  5'-G A T G G G G C T C T T G T T C A T-3'
No. 33.  5'-G A T G G G C C T C A A G T T C A T-3'
No. 34.  5'-G A T G G G C C T C A G G T T C A T-3'
No. 35.  5'-G A T G G G C C T C A C G T T C A T-3'
No. 36.  5'-G A T G G G C C T C A T G T T C A T-3'
No. 37.  5'-G A T G G G C C T C G A G T T C A T-3'
No. 38.  5'-G A T G G G C C T C G G G T T C A T-3'
No. 39.  5'-G A T G G G C C T C G C G T T C A T-3'
No. 40.  5'-G A T G G G C C T C G T G T T C A T-3'
No. 41.  5'-G A T G G G C C T C C A G T T C A T-3'
No. 42.  5'-G A T G G G C C T C C G G T T C A T-3'
No. 43.  5'-G A T G G G C C T C C C G T T C A T-3'
No. 44.  5'-G A T G G G C C T C C T G T T C A T-3'
No. 45.  5'-G A T G G G C C T C T A G T T C A T-3'
No. 46.  5'-G A T G G G C C T C T G G T T C A T-3'
No. 47.  5'-G A T G G G C C T C T C G T T C A T-3'
No. 48.  5'-G A T G G G C C T C T T G T T C A T-3'
No. 49.  5'-G A T G G G T C T C A A G T T C A T-3'
No. 50.  5'-G A T G G G T C T C A G G T T C A T-3'
No. 51.  5'-G A T G G G T C T C A C G T T C A T-3'
No. 52.  5'-G A T G G G T C T C A T G T T C A T-3'
```

-continued

No. 53.  5'-G A T G G G T C T C G A G T T C A T-3'

No. 54.  5'-G A T G G G T C T C G G G T T C A T-3'

No. 55.  5'-G A T G G G T C T C G C G T T C A T-3'

No. 56.  5'-G A T G G G T C T C G T G T T C A T-3'

No. 57.  5'-G A T G G G T C T C C A G T T C A T-3'

No. 58.  5'-G A T G G G T C T C C G G T T C A T-3'

No. 59.  5'-G A T G G G T C T C C C G T T C A T-3'

No. 60.  5'-G A T G G G T C T C C T G T T C A T-3'

No. 61.  5'-G A T G G G T C T C T A G T T C A T-3'

No. 62.  5'-G A T G G G T C T C T G G T T C A T-3'

No. 63.  5'-G A T G G G T C T C T C G T T C A T-3'

No. 64.  5'-G A T G G G T C T C T T G T T C A T-3'

FIG. 1 shows base sequences of DNA probes on the DNA array substrate and an arrangement thereof as well as base sequences of tetramethyl rhodamine labeled model target DNA to be used for subsequent hybridization. The sequence No. 65 (SEQ ID NO: 65) is a target DNA sequence and complementary probe sequences No. 1 to 64 differ each other at three underlined base positions, where one of A, G, C and T comes to create $4^3=64$ combinations. The three base positions of the above described probes correspond to the underlined parts in the sequence No. 65. The position denoted by N in each sequence corresponds to A, G, C and T written above the upper edge of the box. As a result, DNA probe No. 42 is completely complementary to the target DNA, and others have one, two, or three mismatches within the sequences as illustrated in FIG. 1.

(6) A fluorescent dye, fluorescein, was bound to the 5'-terminal of every synthesized DNA probe by using fluorescein phosphoramidite (Glenn Research Co.). In addition, fluorescein was directly bound to another matrix site using fluorescein amidite, at the matrix site, fluorescein was directly coupled with the hydroxy groups of the substrate using fluorescein phosphoramidite instead of amidite in step (2). In this case, elongation reaction will not proceed in principle in subsequent steps.

EXAMPLE 2

Quantitative Fluorometry of the DNA Probe Array Synthesized in Example 1

Fluorescence of the fluorescein in each matrix site was taken in by using a fluorescence microscope ECLIPSE800 (Nikon Corp., an objective lens CFIPlanApo 20×) and a CCD camera C2400-87 equipped with an image intensifier (Hamamatsu Photonics K.K.), then analyzed by an image processing device, Argu50 (Hamamatsu Photonix Co., Ltd.). An amplification degree HV of the image intensifier was 2.0, integration was performed 64 times, and B-2E/C for the fluorescein measurement was employed as a filter block of the fluorescence microscope. In the measurement of the fluorescence, a substrate was placed on a slide glass and 50 mmol/L of a phosphate buffer (pH=7.0, containing 100 mmol/L NaCl) was dropped onto the substrate appropriately, then a cover slip was put thereon for the measurement.

Figure 2:
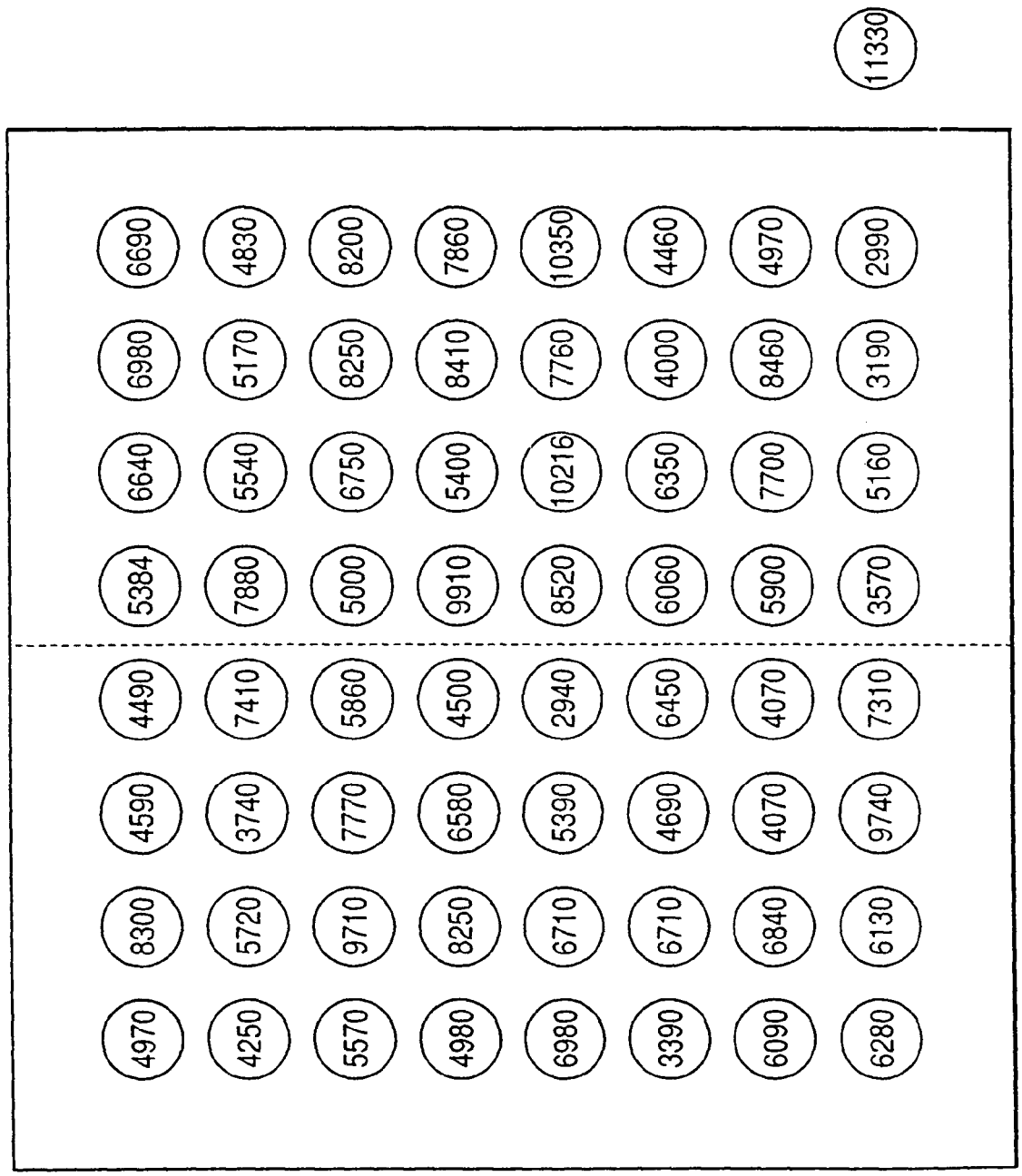
FIG. 2 shows fluorescence values of a DNA probe array of Example 2, derived from fluorescein.

FIG. 2 shows measured fluorescence values. The fluorescence value (11330) written outside the square in FIG. 2 was from a matrix site where the fluorescein was directly bound to the substrate. FIG. 2 shows that fluorescence values obtained from the bonded oligonucleotides range from 2940 to 10350. These values can be used to correct the amounts of respective oligonucleotide probes, and the hybridization results can be corrected by using these fluorescence values. When a plurality of DNA arrays are used, it is possible to correct the values of the matrix sites using the fluorescence value of the control matrix site where fluorescein has been directly bonded to the substrate in respective DNA arrays.

EXAMPLE 3

Assay of a Target DNA Using the DNA Probe Array Synthesized in Example 1

Figure 3:
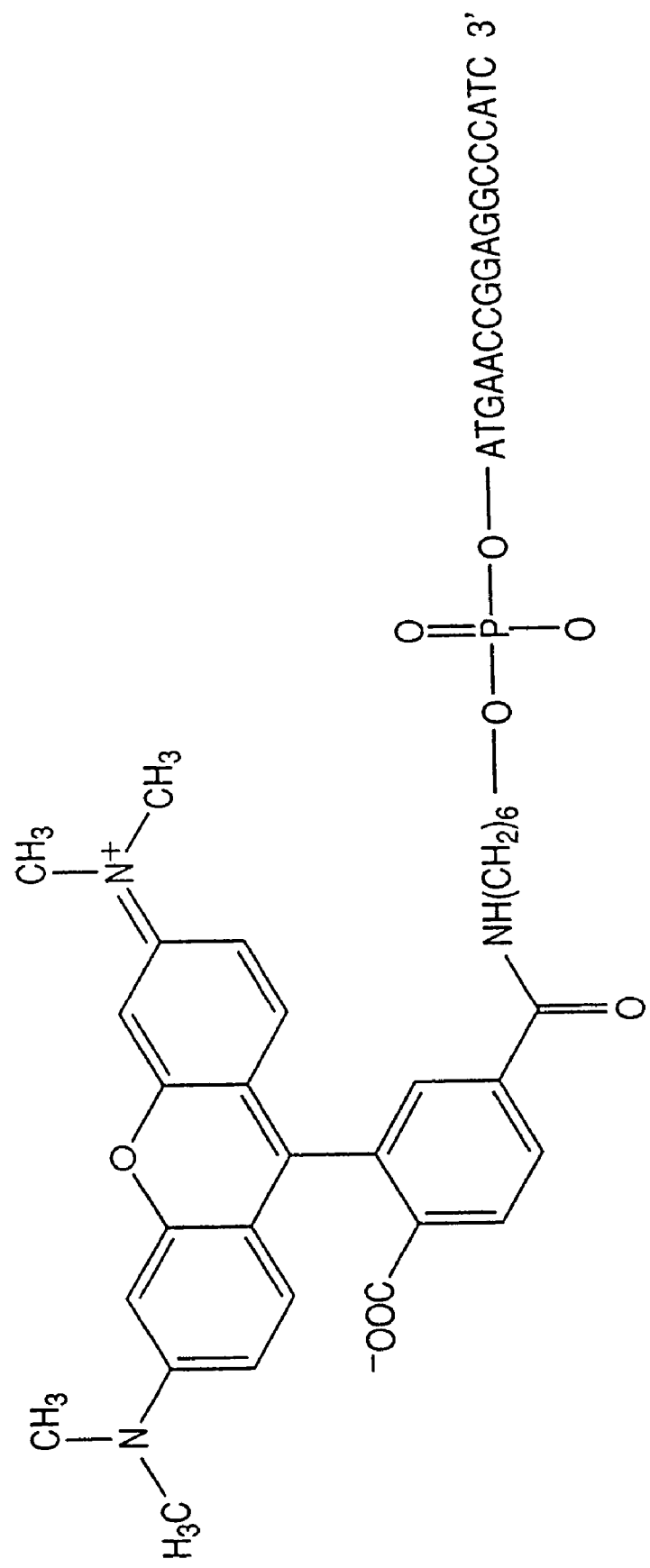
FIG. 3 shows the structural formula of a target DNA.

FIG. 3 shows a structure of a tetramethyl rhodamine-labeled model target DNA used for hybridization. This target DNA sequence corresponds to the sequence No. 65 as mentioned above.

The above described probe array was dipped in a 50 mmol/L phosphate buffer (pH=7.0, containing 100 mmol/L of NaCl and 2% bovine serum albumin (Sigma-Aldrich Japan) for one hour, then rinsed with the above described buffer appropriately, and subjected to hybridization.

The hybridization was carried as follows:

First the DNA probe array and 2 mL of a 50 mmol/L phosphate buffer (pH=7.0, 100 mmol/L NaCl) containing the above described target DNA at a concentration of 50 nmol/L were enclosed in a resin pack for hybridization, and heated to 70° C. and then cooled to 20° C., and left standing for 24 hours.

Next, the substrate was rinsed in the above buffer for 20 minutes, then fluorescence from tetramethyl rhodamine of the target DNA was measured in the same manner as in Example 2. In this case, Y-2E/C was employed as a fluorescence filter block. In addition, the amplification degree of the image intensifier was 4.0.

The result is shown in FIG. 4. FIG. 5 shows values after correction obtained by multiplying the measured values of FIG. 4 by a correction coefficient (control fluorescence value from fluorescein directly bonded to the substrate without elongation reaction 11330/measured fluorescence from fluorescein at the corresponding matrix site where elongation reaction had been carried out). These values are compared with values obtained from Comparative Examples (as described later).

COMPARATIVE EXAMPLE 1

Application of Synthesized DNA Probes to a Substrate by Ink-Jet Process, Probe Coupling and Hybridization A glass substrate was cleaned as described in Example 1. An 1% aqueous solution of aminosilane coupling agent (KBM-603, Shin-Etsu Chemical Co., Ltd.) purified by vacuum distillation was stirred for one hour at room temperature to hydrolyze the methoxy moiety thereof. The above treated substrate was rinsed and immediately dipped in the above described aqueous solution of silane coupling agent for one hour at room temperature. Then the substrate was rinsed with running water (ultra pure water), dried by blowing nitrogen gas, and then fixed in an oven for one hour at 120° C.

After cooling, the substrate was dipped in a 0.3% solution (ethanol:dimethylsulphoxide=1:1) of N-(6-maleimidocaproxy)succiimide (EMCS, Dojindo Co.) (Compound I below) for two hours at room temperature for reaction, and then it was rinsed with a solution of ethanol:dimethylsulphoxide=1:1 once and rinsed with ethanol three times, and dried by blowing nitrogen gas.

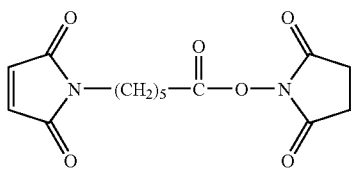

Compound I

This treatment coupled the amino group of the silane coupling agent on the glass substrate and the succiimide group of EMCS, so that a maleimide group was formed on the substrate surface. This maleimide group is coupled to the thiol group of a DNA probe (as described later).

Sixty four kinds of DNA probes having completely the same sequences as described in Example 3 were purchased from Becks K.K. Each of these DNAs carries a thiol linker at 5'-terminal thereof for coupling to the substrate. An example of the DNA having the thiol linker is illustrated as Compound II below.

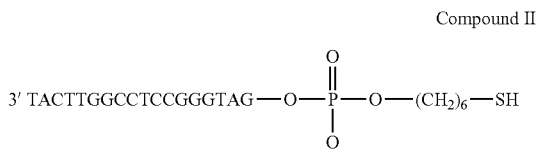

Compound II

This compound II has a base sequence (No. 42) which is completely complementary to the model target DNA.

Each DNA probe was dissolved in a solvent to be ejected from a thermal jet printer, that is, each DNA probe was dissolved in an aqueous solution containing 7.5 wt % of glycerin, 7.5 wt % of urea, 7.5 wt % of thiodiglycol, and 1 wt % of acetylene alcohol represented by the following general formula III (trade name: Acetylenol EH, Kawaken Fine Chemicals Co., Ltd.) to an absorbance of 1.0.

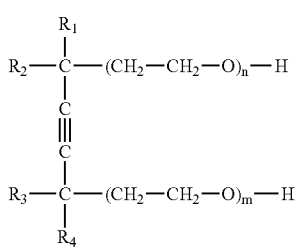

Compound III

Then 0.4 mL of each solution was charged in a modified ink supplying part of a thermal jet printer, which printer can hold two ink-jet heads (Canon Inc.). Then the solutions were discharged onto the above described substrate to form the same pattern as in Examples 1 to 3 with different shapes. According to the configuration of this apparatus, the amount of one drop of the discharged solution was 24 pL, and the dot diameter formed by one drop of the solution became 70 to 100 μm under these conditions. The discharging density was 120 dpi (dot/inch). After probe application, the substrate was placed in a moisture chamber at 100% humidity for one hour at room temperature for reaction, then rinsed with running water (ultra pure water) for 30 seconds.

Treatment with BSA, conditions for hybridization, and conditions of quantitative fluorometry were the same as described in Example 3. Amplification degree of the image intensifier was 2.0. The result of quantitative fluorometry is shown in FIG. 6.

FIG. 7 shows the comparison of the results of FIG. 5 and the results of FIG. 6. The former shows the corrected hybridization results obtained by using an array of DNA probes sequentially synthesized and terminal labeled, corrected by the fluorescence value of the fluorescent dye used for labeling the probe terminus and the fluorescent value of the fluorescent dye directly bonded to the substrate, and the latter shows the hybridization results obtained by using a DNA probe array where the synthesized and purified probes were bonded to the substrate.

Value $Cn$ in the matrix of FIG. 7 was calculated by the following equation (1), where $An$ is a value from each matrix site of FIG. 5 and $Bn$ is a value from each matrix site of FIG. 6 ($n=1$ to 64).

$$Cn = Bn \times (\Sigma An / \Sigma Bn) / An \tag{1}$$

($\Sigma An$ represents a sum of A1 to A64 and $\Sigma Bn$ represents a sum of B1 to B64.)

FIG. 7 shows the effectiveness of the correction of the present invention. Values indicated in FIG. 7 are within a range of ±20% and the standard deviation is within a range of about 9%. It is also possible to correct data of plural DNA probe arrays on the basis of fluorescence values of control matrix sites where no elongation reaction was carried out and a fluorescent dye (fluorescein) was directly bonded to the substrate.

As described above, according to the present invention, one can evaluate the probe amount at each matrix site by terminal labeling of the sequentially synthesized probes. Also it enables to detect and quantify the target substance by correcting respective probe amounts. Further, direct coupling of a labeling substance to the substrate enables correction between probe arrays.

What is claimed is:

1. A method of evaluating an amount of a target substance comprising the steps of:

reacting a probe away and the target substance which is previously labeled, wherein the probe array comprises a plurality of probes immobilized at a plurality of matrix sites on a substrate for capturing the target substance, the plurality of probes is sequentially synthesized at the plurality of matrix sites on the substrate to a desired length, each of the plurality of probes is different from each other, and a labeling compound is coupled to each terminus of the plurality of probes in a final step of the sequential synthesis;

measuring an amount of the labeling compound at each of the plurality of matrix sites to determine an amount of the probe at each of the plurality of matrix sites;

measuring an amount of the labeled target substance captured by the probe at each of the plurality of matrix sites;

measuring an amount of the labeling compound directly bonded to the substrate at a predetermined matrix site on the surface of the substrate, wherein no probes are immobilized at the predetermined matrix site, and wherein the labeling compound is directly bonded to the substrate during a first step of the sequential synthesis without an elongation reaction;

comparing the amount of the probe, the amount of the labeled target substance, and the amount of the directly bonded labeling compound, wherein all probes forming the probe array have the labeling compound coupled to their termini.

2. The method according to claim 1, further comprising a step of correcting the amount of the labeled target substance based on the comparison between the amount of the probe, the amount of the labeled target substance, and the amount of the directly bonded labeling compound.

* * * * *

UNITED STATES PATENT AND TRADEMARK OFFICE
CERTIFICATE OF CORRECTION

PATENT NO. : 7,402,384 B2  Page 1 of 1
APPLICATION NO. : 10/634510
DATED : July 22, 2008
INVENTOR(S) : Tadashi Okamoto et al.

It is certified that error appears in the above-identified patent and that said Letters Patent is hereby corrected as shown below:

COLUMN 1:
    Line 12, "an" should read -- a --; and
    Line 65, "100%, some times" should read -- 100%; sometimes --.

COLUMN 2:
    Line 15, "above" should read -- above- --.

COLUMN 3:
    Line 18, "an" should read -- a --.

COLUMN 7:
    Line 27, "differ" should read -- differ from --; and
    Line 30, "above described" should read -- above-described --.

COLUMN 31:
    Line 4, "away" should read -- array --.

COLUMN 32:
    Line 7, "reaction;" should read -- reaction; and --.

Signed and Sealed this

Third Day of March, 2009

JOHN DOLL
*Acting Director of the United States Patent and Trademark Office*